(12) United States Patent
Trcka et al.

(10) Patent No.: US 10,215,880 B1
(45) Date of Patent: Feb. 26, 2019

(54) PULSED NEUTRON DETERMINATION OF GRAVEL PACK DENSITY

(71) Applicant: Weatherford Technology Holdings, LLC, Houston, TX (US)

(72) Inventors: Darryl E. Trcka, Burnsville, NC (US); Steve Riley, Spring, TX (US)

(73) Assignee: Weatherford Technology Holdings, LLC, Houston, TX (US)

( * ) Notice: Subject to any disclaimer, the term of this patent is extended or adjusted under 35 U.S.C. 154(b) by 0 days.

(21) Appl. No.: 15/725,051

(22) Filed: Oct. 4, 2017

(51) Int. Cl.
*G01V 5/04* (2006.01)
*G01V 5/10* (2006.01)
*E21B 49/00* (2006.01)
*G01N 23/00* (2006.01)

(52) U.S. Cl.
CPC .............. *G01V 5/10* (2013.01); *E21B 49/003* (2013.01); *E21B 49/005* (2013.01); *G01N 23/005* (2013.01)

(58) Field of Classification Search
CPC ........................................................ G01V 5/12
See application file for complete search history.

(56) References Cited

U.S. PATENT DOCUMENTS

| | | | |
|---|---|---|---|
| 3,925,659 A | 12/1975 | Paap et al. | |
| 4,008,392 A | 2/1977 | Lock et al. | |
| 4,587,423 A | 5/1986 | Boyce | |
| 4,950,892 A * | 8/1990 | Olesen | E21B 43/04 250/269.7 |
| 5,440,118 A | 8/1995 | Roscoe | |
| 5,481,105 A | 1/1996 | Gold | |
| 6,044,327 A * | 3/2000 | Goldman | G01V 1/50 702/11 |
| 6,552,333 B1 * | 4/2003 | Storm | G01V 5/12 250/265 |
| 6,554,065 B2 * | 4/2003 | Fisher | E21B 43/04 166/250.02 |
| 7,059,404 B2 * | 6/2006 | Flecker | E21B 43/04 166/250.02 |
| 7,520,326 B1 * | 4/2009 | Hill | E21B 43/045 166/144 |
| 7,999,220 B2 | 8/2011 | Odom | |
| 2003/0213898 A1 | 11/2003 | Storm et al. | |
| 2004/0051650 A1 * | 3/2004 | Gonsoulin | G01V 11/002 340/853.1 |
| 2005/0067563 A1 * | 3/2005 | Gilchrist | G01V 5/102 250/269.7 |
| 2008/0251710 A1 | 10/2008 | Riley et al. | |
| 2010/0017134 A1 | 1/2010 | Steinman et al. | |

OTHER PUBLICATIONS

Email correspondence from inventor Stephen Riley, dated Feb. 19, 2018, 1 page.

* cited by examiner

*Primary Examiner* — Kiho Kim
(74) *Attorney, Agent, or Firm* — Lewis & Reese, PLLC

(57) ABSTRACT

Methods and systems for quantitatively determining pack density within a section of a wellbore are disclosed. The method compares acquired pulsed neutron measurements to models of the section having zero pack density and one hundred percent pack density and extrapolates the measured pulsed neutron data between those two extremes to quantitatively determine pack density. The methods and systems allow hydrocarbon saturation and pack density to be determined in a single trip of a pulsed neutron tool.

13 Claims, 8 Drawing Sheets

US 10,215,880 B1

PULSED NEUTRON DETERMINATION OF GRAVEL PACK DENSITY

FIELD OF THE INVENTION

The present application relates to wellbore logging, and more particularly to logging wellbores to determine gravel pack density.

BACKGROUND

FIG. 1A illustrates a portion of a hydrocarbon well 100 extending through an interval of a subterranean formation 101. The well comprises a production tubing 103 and an annulus 102 around the production tubing. If the formation 101 contains unconsolidated particles, such as sand, produced fluids from the formation can carry those particles into the annulus 102, where the particles can enter the production tubing 103 and abrade or clog production equipment. The particles can also cause wellbore damage by clogging producing formations.

Well operators/service providers can place gravel packs within the wellbore to prevent formation particles from entering the wellbore and damaging the wellbore or equipment. Gravel packs comprise relatively coarse particulate material, such as graded sand, gravel or proppant. The gravel pack can be placed within the annulus of wellbore against the unconsolidated (or poorly consolidated) formation to form a barrier to formation particulate entering the wellbore.

FIG. 1A shows a gravel pack 104 placed against the formation 101 within the annulus 102 of the illustrated interval of the wellbore 100. The gravel pack 104 is held in place by a screen 105. The screen 105 is perforated with openings sized to exclude the gravel pack 104 material but to allow formation fluids to enter the annulus 102. The process of placing a gravel pack within an interval of a wellbore, known as "gravel pack completion," is not relevant to this disclosure and will not be discussed.

The section of the wellbore 100 illustrated in FIG. 1A is referred to as an "open hole" wellbore, meaning that the wellbore does not contain a casing. FIG. 1B illustrates a section of cased wellbore 110. The cased wellbore 110 contains a casing 106 cemented in place by cement 107. The casing 106, cement 107, and a portion of the formation 101 have been perforated by perforations 108, as is known in the art. Following the perforation operation, a gravel pack 104 and screen 105 have been installed in the wellbore to prevent unconsolidated particles from entering the annulus 102.

Ideally, a gravel pack 104 would remain uniformly distributed throughout the life of the well. However, non-uniformities within the gravel pack may occur during gravel pack completion or may develop over time. Such non-uniformities can adversely impact the effectiveness of the gravel pack, especially if voids within the gravel pack allow formation fluids to enter the annulus.

Well operators evaluate the uniformity and porosity of their gravel packs using a process known as "gravel pack density logging." Gravel pack density logging generally involves using a wireline to run a tool into the wellbore. Various types of density logging tools exist. Several types of density logging tools use a radiation source to irradiate the gravel pack and the surrounding formation (or to induce radiation within the gravel pack and/or formation, as described below). Such tools also include one or more detectors to detect radiation back-scattered from the gravel pack, formation, and/or materials in the annulus to evaluate the density of the gravel pack. Generally, when the gravel pack is less dense, a greater amount of radiation will be received at the detector. A denser (i.e., less porous) gravel pack captures more of the backscattered radiation, preventing it from reaching the detector.

Gravel pack density logging tools, as described above, can determine the relative density or porosity of a gravel pack, but do not provide quantitative measurements. In other words, the tool can indicate that one location is more or less dense than another location, but is incapable of providing an absolute density value for either location. Thus, there is a need in the art for gravel pack density logging tools and methods that can provide quantitative information about the density of gravel packs.

DESCRIPTION

The inventors have developed a pulsed neutron logging method for quantitatively determining gravel pack density within a wellbore. The method and tools for executing the method are described herein. Aspects of pulsed neutron logging are explained first as an aid to understanding the method and tools for quantitative gravel pack density measurements.

Figure 1B:
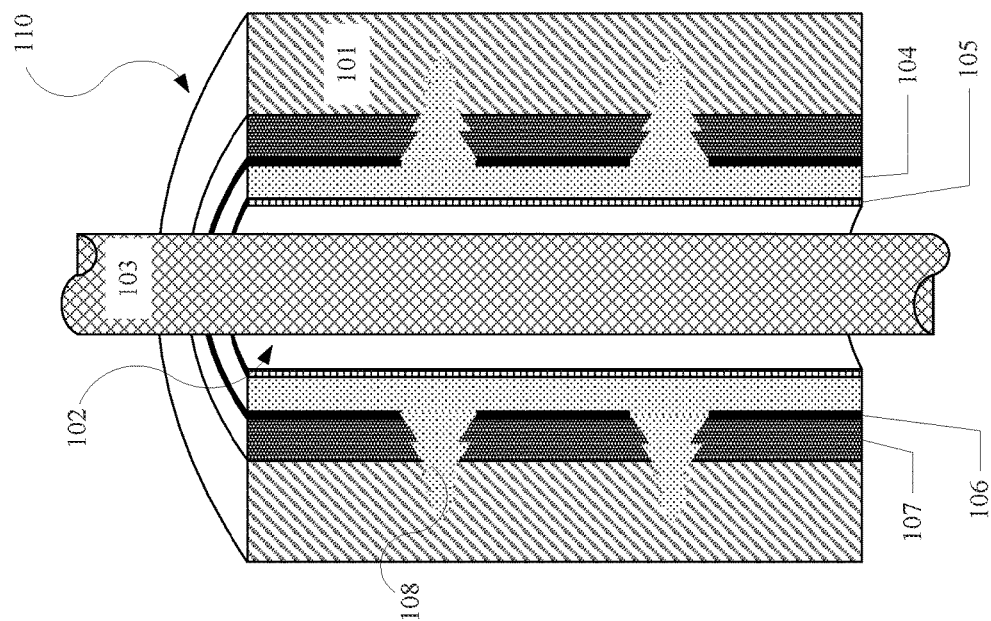
FIGS. 1A and 1B show a wellbore having a screen and a pack.
Figure 1A:
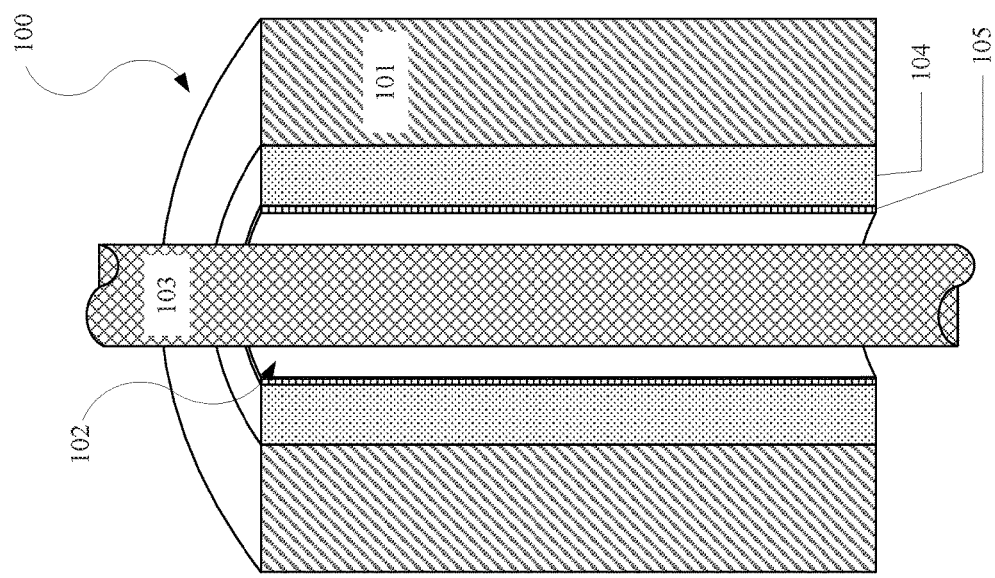
Figure 2:
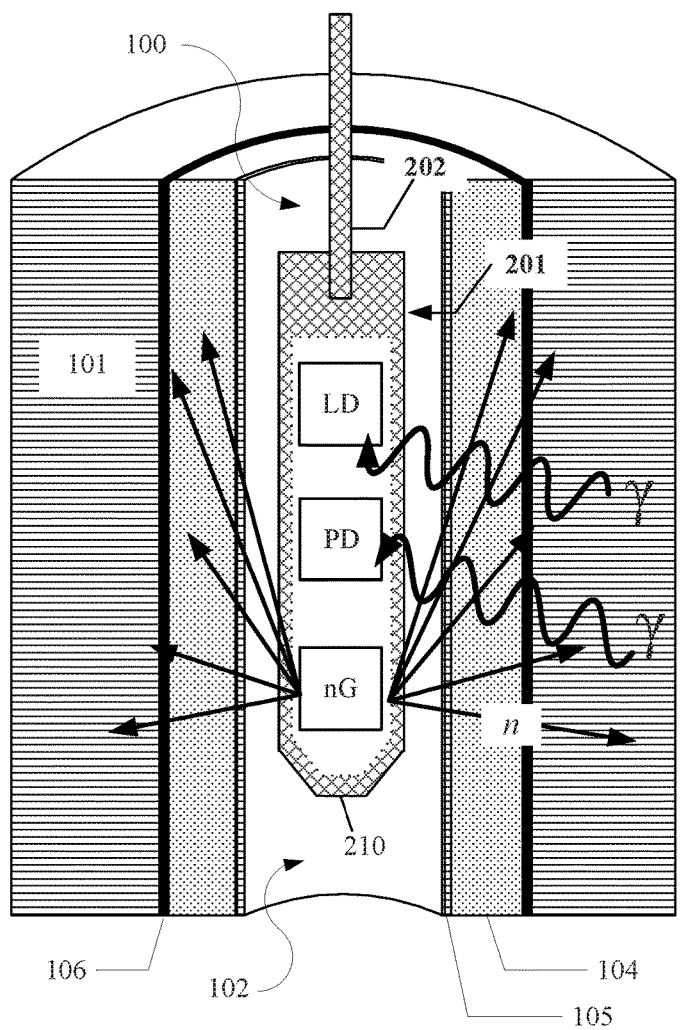
FIG. 2 shows a pulsed neutron tool.

FIG. 2 illustrates a pulsed neutron tool, more generally referred to herein as a sonde 201. The sonde includes a sealed housing 210, which contains a neutron generator, two or more detectors, and instrumentation, as described below. The neutron generator is labeled nG, and the detectors are labeled PD (proximal detector) and LD (long detector) in FIG. 2. The sonde 201 can be lowered into the wellbore 102 using a wireline 202, which supports and conveys the sonde 201 and provides electrical power and communication between the sonde 201 and the surface. Machinery and additional instrumentation may be located at the surface to control the deployment and recovery of the sonde 201 and to send data to and from the sonde via the wireline 202.

The neutron generator nG can generate neutrons. The generated neutrons have high energy, typically greater than 10 MeV. One type of neutron generator comprises a device that accelerates deuterium ($^2$D) and tritium ($^3$T) ions toward a target that also contains $^2$D and $^3$T. The collision produces neutrons, which are ejected from the neutron generator nG with about 14 MeV of energy.

The sonde 201 also encloses two or more gamma detectors. The illustrated sonde includes two detectors—a proximal detector PD and long detector LD. Gamma detectors are also well known in the art and typically comprise a material that absorbs gamma photons causing the material to emit visible or ultraviolet photons. Such a material is referred to as a scintillator material. Examples of scintillator materials include sodium iodide, bismuth germanate, and lanthanum bromide-based materials, such as cesium-doped lanthanum bromide. The scintillator material is positioned proximate to a photomultiplier tube (PMT), which detects the emitted visible or ultraviolet photon and generates an electric in response. The electric signal can be processed to determine the number and energy of the gamma photons that reach the detector.

The sonde 201 also encloses electronics such as control circuits and power circuits (not shown) that operate and control the elements of sonde. The sonde 201 also includes a telemetry subsection (not shown) that encloses communications control and transmission electronics for telemetering data between the sonde 201 and the surface. Such circuitry and telemetry is well known in the art and is not discussed here.

During a pulsed neutron measurement, the neutron generator nG generates neutrons, which are released from the pulsed neutron tool 201 at typically about 14 MeV, a very high energy. The neutrons are represented as straight arrows labeled n in FIG. 2. The high-energy neutrons can undergo a variety of interactions with matter in the annulus 102, the casing 105, the gravel pack 104, and the formation 101.

Figure 3:
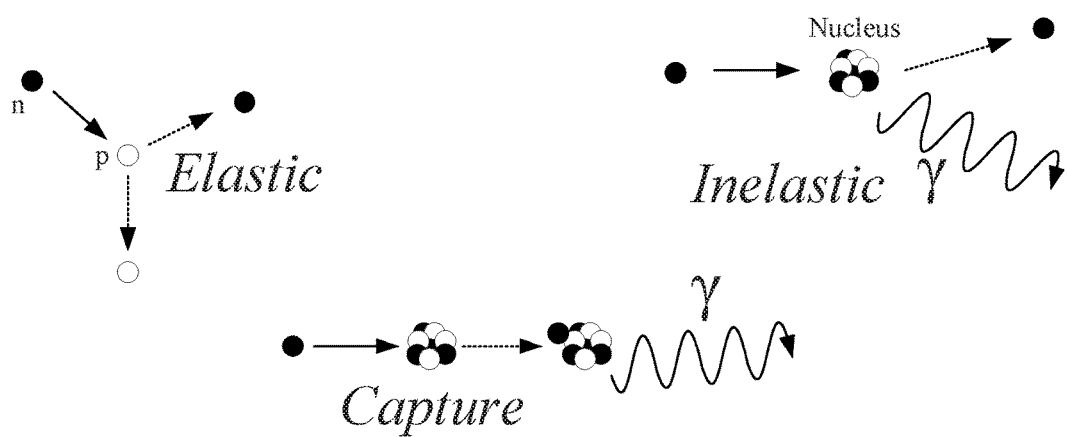
FIG. 3 illustrates three modes of scattering.

FIG. 3 illustrates three types of such interactions. One possible interaction is an elastic collision (a.k.a. elastic scattering) between a neutron n and a nucleus. In the illustrated example, the neutron n collides with a hydrogen nucleus, which consists of a single proton p. The neutron n imparts some of its energy to the proton p causing the proton to gain energy and the neutron to lose energy. Elastic scattering can be thought of as being like billiard balls colliding.

Another typed of interaction is an inelastic collision (a.k.a. inelastic scattering). During an inelastic collision, a neutron collides with a nucleus, imparting a portion of the neutron's energy to the nucleus. Thus, the neutron exits the collision with less energy than before. The energy that the neutron imparts to the nucleus excites the nucleus, meaning that the imparted energy causes the nucleus to transition from a low energy state (a.k.a. ground state) to a high-energy state (a.k.a. excited state). After a given time, the nucleus relaxes from the excited state back to the ground state and may emit a gamma ($\gamma$) photon during the relaxation process. Nuclei of different atoms emit gamma photons having different energies during such a process.

Notice that both elastic and inelastic scattering cause neutrons to lose energy. After a high-energy neutron has undergone a number of elastic or inelastic collisions, the neutron's energy may be reduced to about 0.025 eV. Such neutrons are referred to as "thermal neutrons." Thermal neutrons can participate in a third type of interaction whereby a thermal neutron is "captured" by the nucleus of a larger atom. When a nucleus captures a thermal neutron, the capturing nucleus is excited from a low energy state to a high-energy state to a high-energy state. The excited nucleus may emit a gamma photon when it relaxes back to the low energy state. The energy of the emitted gamma photon is characteristic of the particular type of nucleus involved in the neutron capture interaction.

The nuclei of some atoms that may be present near a wellbore have a greater propensity to capture thermal neutrons than other nuclei. A nuclei's propensity to capture a neutron is referred to as the nuclei's "neutron capture cross-section" and is abbreviated $\Sigma$. Chlorine has a high capture cross-section, meaning that it has a relatively high affinity for capturing thermal neutrons. Since chlorine is present in salt water, the rate at which neutrons are captured can be an indicator of the amount of salt water present in a formation—a measurement referred to as sigma ($\Sigma$) logging.

Two of the three neutron-atom interactions illustrated in FIG. 3—inelastic scattering and neutron capture—cause gamma photons to be emitted. Moreover, the energy of the emitted gamma photons is indicative of the type of atoms involved in the interaction. For example, when carbon atoms are bombarded with high energy neutrons they undergo inelastic scattering and emit gamma photons having about 4 eV of energy. Likewise, oxygen emits gamma photons having about 6 eV of energy due to inelastic scattering. Silicon atoms undergo thermal neutron capture, causing the silicon nucleus to emit 3.0-4.7 eV gamma photons. Calcium atoms emit 4.7-6.4 eV photons due to neutron capture. A service provider can determine the presence and relative amounts of carbon, oxygen, silicon, and calcium in a measured region of a formation by irradiating the region with neutrons and counting the number of gamma photons emitted at those characteristic energies. Such measurements are valuable because carbon is indicative of hydrocarbons, oxygen is indicative of water, silicon is indicative of sandstone, and calcium is indicative of limestone. Thus, pulsed neutron measurements can yield information about the relative amounts of water and oil present in a formation as well as the lithology of the formation.

Pulsed neutron measurements of a well can be interpreted based on a computer model of the well. The model may include parameters such as hole size; casing size; porosity, lithology; borehole fluid density, salinity, and composition; and the presence of tubing strings. Those parameters may be known at each depth from the drilling and completion process and/or other logging measurements for the positions (depths) within the well being investigated. The model simulates how the pulsed neutron tool should respond under various conditions within the well being logged. Modeling techniques for modeling pulsed neutron responses under various conditions are known in the art. One example is Monte Carlo modeling techniques. Once the pulsed neutron responses for a well have been modeled, the real measurements can be compared to the model to determine the real properties of the well.

Figure 4:
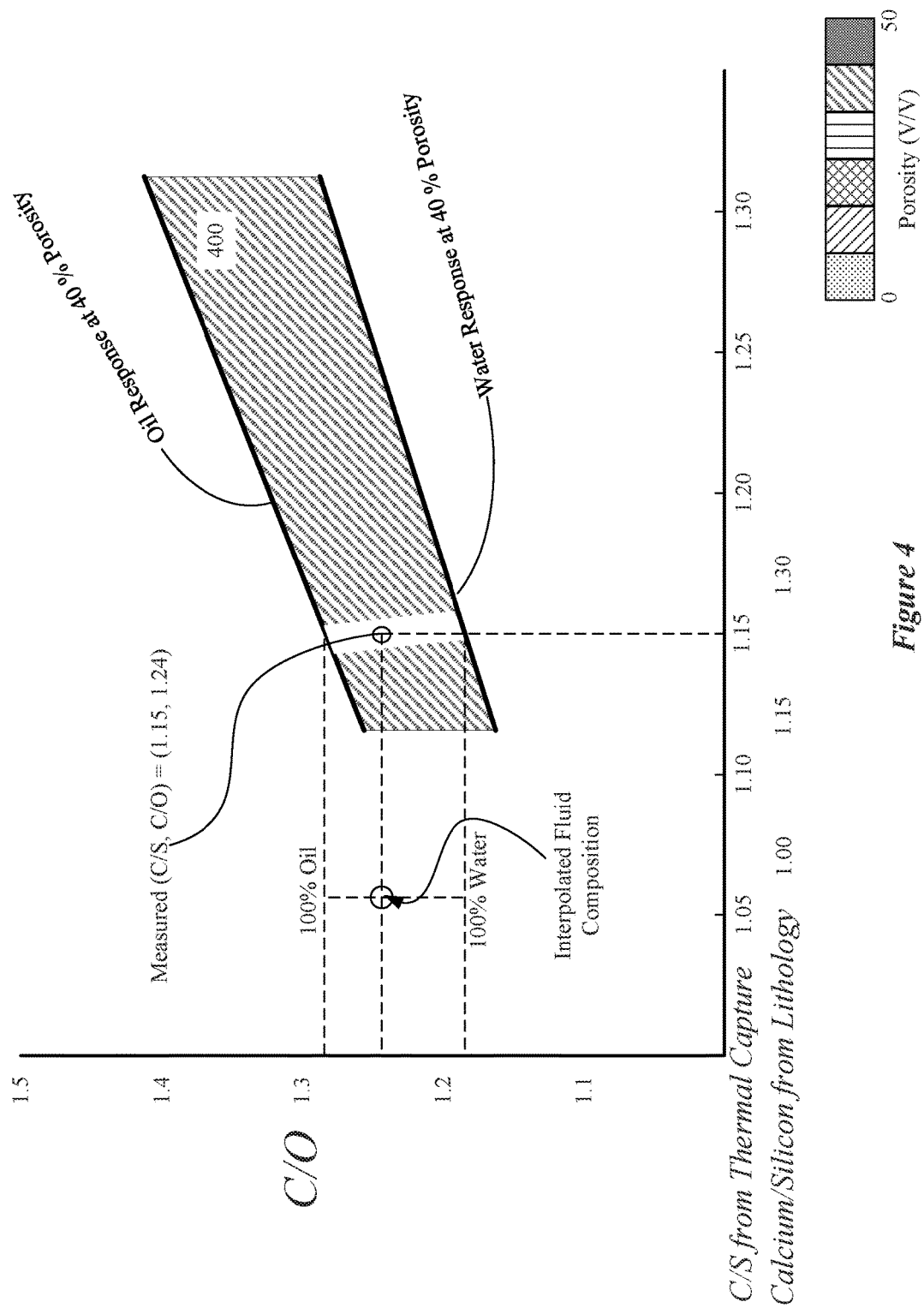
FIG. 4 shows a modeled data set for a pulsed neutron measurement.

FIG. 4 illustrates a modeled data set 400 of pulsed neutron responses in a formation. The modeled ratio of gamma photon counts characteristic of calcium and silicon (C/S) are plotted on the horizontal axis. The modeled C/S count numbers depend on the well's parameters noted above, and particularly on the formation porosity of the formation. Data sets, such as data set 400 must be generated for each formation porosity of interest. For the sake of discussion, assume that data set 400 corresponds to a porosity of 40%.

For each C/S value, the model calculates a carbon to oxygen count ratio (C/O) corresponding to a condition wherein the pores of the formation are 100% filled with hydrocarbon and for a condition wherein the pores are 100% filed with water. The carbon to oxygen ratios (C/O) are plotted on the vertical axis. The line defining the top of the shaded area of the data set 400 corresponds the gamma photon signals that would be expected if the fluid contained in the formation is 100% oil. The line defining the bottom of the shaded area corresponds the gamma photon signals that would be expected in if the fluid contained in the pores of that formation is 100% water. The 100% oil and 100% water lines define the boundary conditions for the modeled porosity. The ratio of oil to water in a mixture can be determined for a given C/S value by extrapolating between the boundary lines at that C/S value. It should be noted that the extrapolation between the two 100% values may or may not be based on a linear extrapolation. The extrapolation function can be refined by modeling additional fluid compositions between the 100% values. Such modeling is known to persons of skill in the art.

Actual pulsed neutron measurements can be correlated to the modeled data for a given porosity once the model is calculated. The pulsed neutron tool can be configured to acquire pulsed neutrons indicative of carbon, oxygen, calcium, and silicon in a single trip. Assume, for example, that a pulsed neutron measurement in the interval of formation yields a ratio of calcium to silicon gamma photon counts C/S of 1.5 and a ratio of carbon to oxygen counts C/O of 1.24. Correlating the measured C/S ratio to the model indicates the position on the horizontal axis to extrapolate fluid composition. At the 1.5 position on the horizontal axis, the value expected for 100% oil is about 1.27 and the value expected for 100% water is about 1.17. Extrapolating between the two 100% values yields the fluid composition that corresponds to the measured C/O gamma photon count of 1.24.

Figure 5:
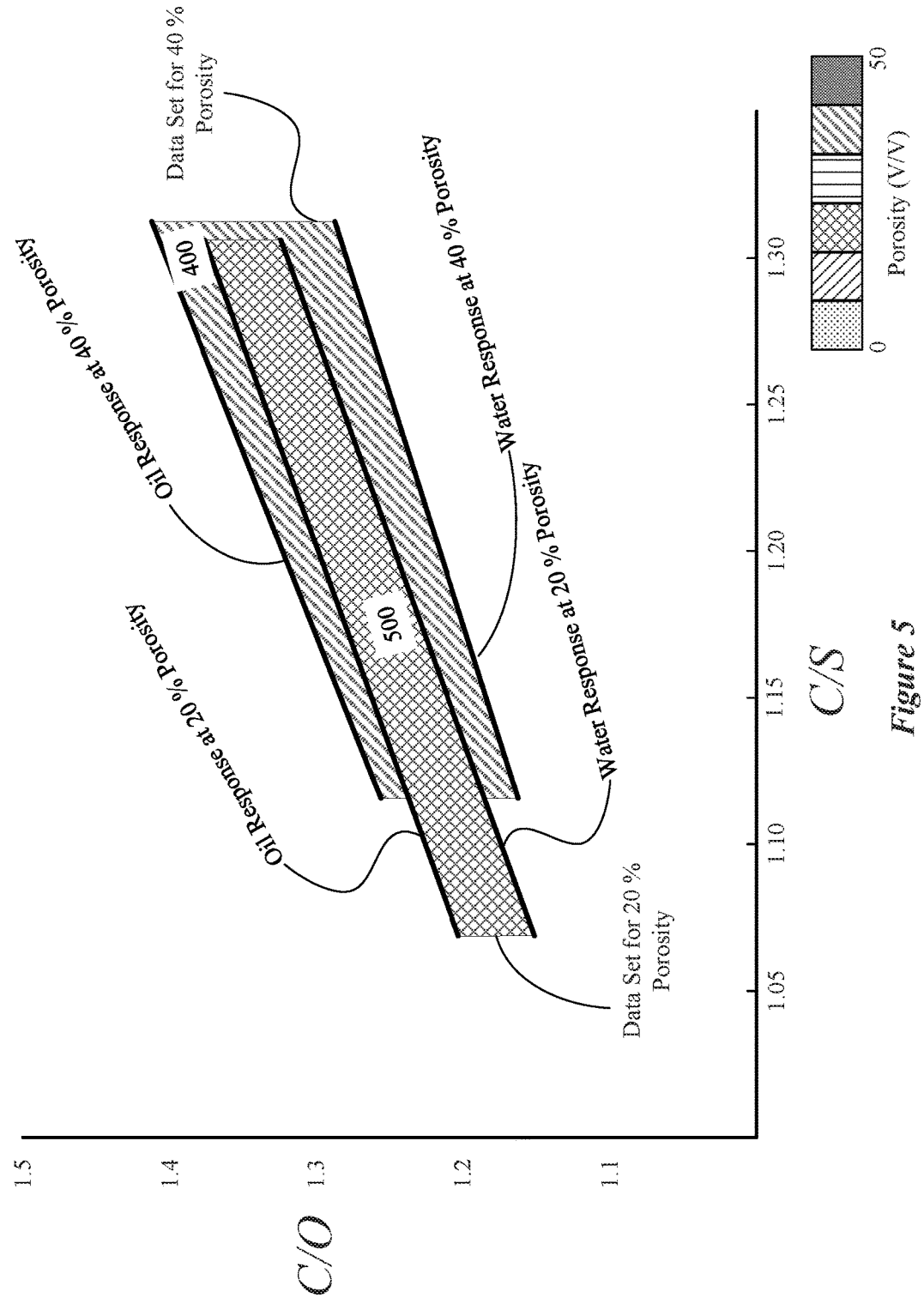
FIG. 5 shows modeled data sets for pulsed neutron measurements in formations having different porosities.

As mentioned above, the modeled data set 400 is for the formation porosity of 40%. As the formation porosity is likely different at different positions within the formation, multiple porosities must be modeled. FIG. 5 illustrates an additional data set 500 modeled for 20% porosity overlaid upon the 40% porosity data set 400. Since a well service provider knows the formation porosity at every depth within a well (based on logging while drilling data, for example), they can model the pulsed neutron response characteristics for all the relevant porosities.

Figure 6:
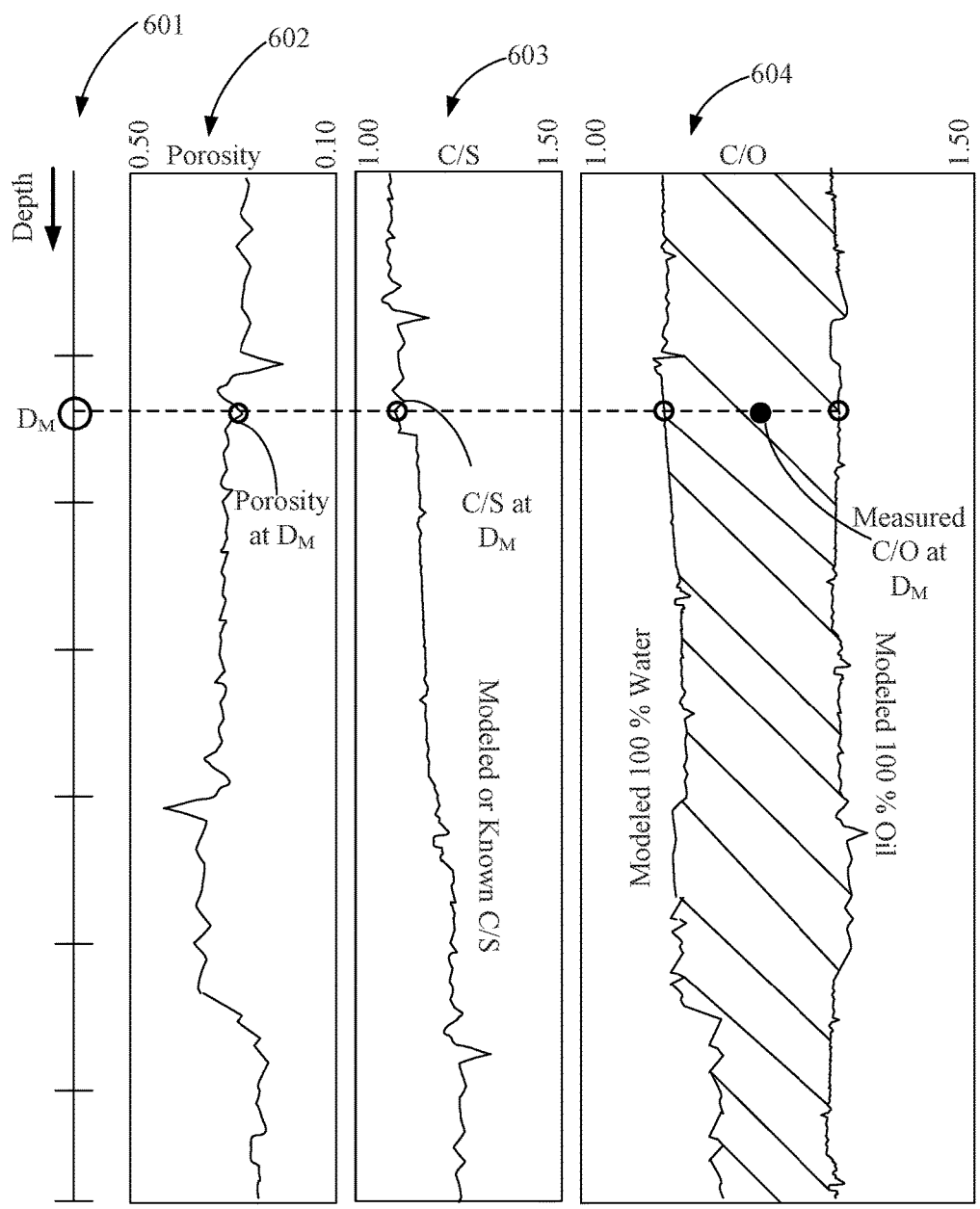
FIG. 6 shows modeled and measured pulsed neutron measurements as a function of depth.

The modeled C/S and C/O pulsed neutron responses for the various porosities can be merged with depth-porosity data, as illustrated in FIG. 6. FIG. 6 shows depth plotted vertically 601. Porosity 602, which is known from previous measurements, is plotted as a function of depth. The measured or modeled C/S ratio 603 can also be correlated to depth. According to some embodiments, lithology is known for each depth and the modeled C/S ratio for the corresponding lithology can be plotted as a function of depth. Alternatively, the C/S ratio may be measured and correlated to lithology using modeled parameters. In either case, a C/S ratio 603 can be plotted as a function of depth.

The C/S ratios and porosities at each depth are then correlated to the modeled C/O ratios corresponding to 100% oil and 100% water at each depth using the modeled data sets, as shown in FIGS. 4 and 5. The 100% oil and 100% water ratios at each depth define an envelope of possible C/O gamma counts 604. The oil/water ratio at each depth can be determined by interpolating between the boundaries of that envelope.

Assume that a pulsed neutron measurement at a depth within a wellbore $D_M$ yields a ratio of calcium-silicon gamma counts $(C/S)_{DM}$ and a ratio carbon-oxygen gamma counts $(C/O)_{DM}$. Since known porosity at the depth $D_M$ determines which data set accurately correlates the measured $(C/S)_{DM}$ to expected C/O values for 100% oil and for 100% water. For example, if the known porosity at the depth $D_M$ is 40%, then data set 400 will be used; if the porosity is 20%, then data set 500 will be used (see FIG. 5), etc. Using the appropriate data set, the measured $(C/S)_{DM}$ value is correlated to an expected 100% oil C/O value and an expected 100% water C/O value, as illustrated in FIG. 4. Those two expected C/O values provide an envelope that contains the measured $(C/O)_{DM}$ value. Extrapolation yields a measured fluid composition at the depth $D_M$. The process can be repeated at any depth within the well.

The inventors have discovered that by including parameters relating to gravel pack density in the modeling of the pulsed neutron responses under various conditions, it is possible to obtain quantitative gravel pack density measurements. Assuming the gravel pack largely comprises silicon-based material, pulsed neutron measurements in a wellbore of a given porosity having a full gravel pack will generally be shifted to lower C/S values compared to the same wellbore with no gravel pack.

Figure 7:
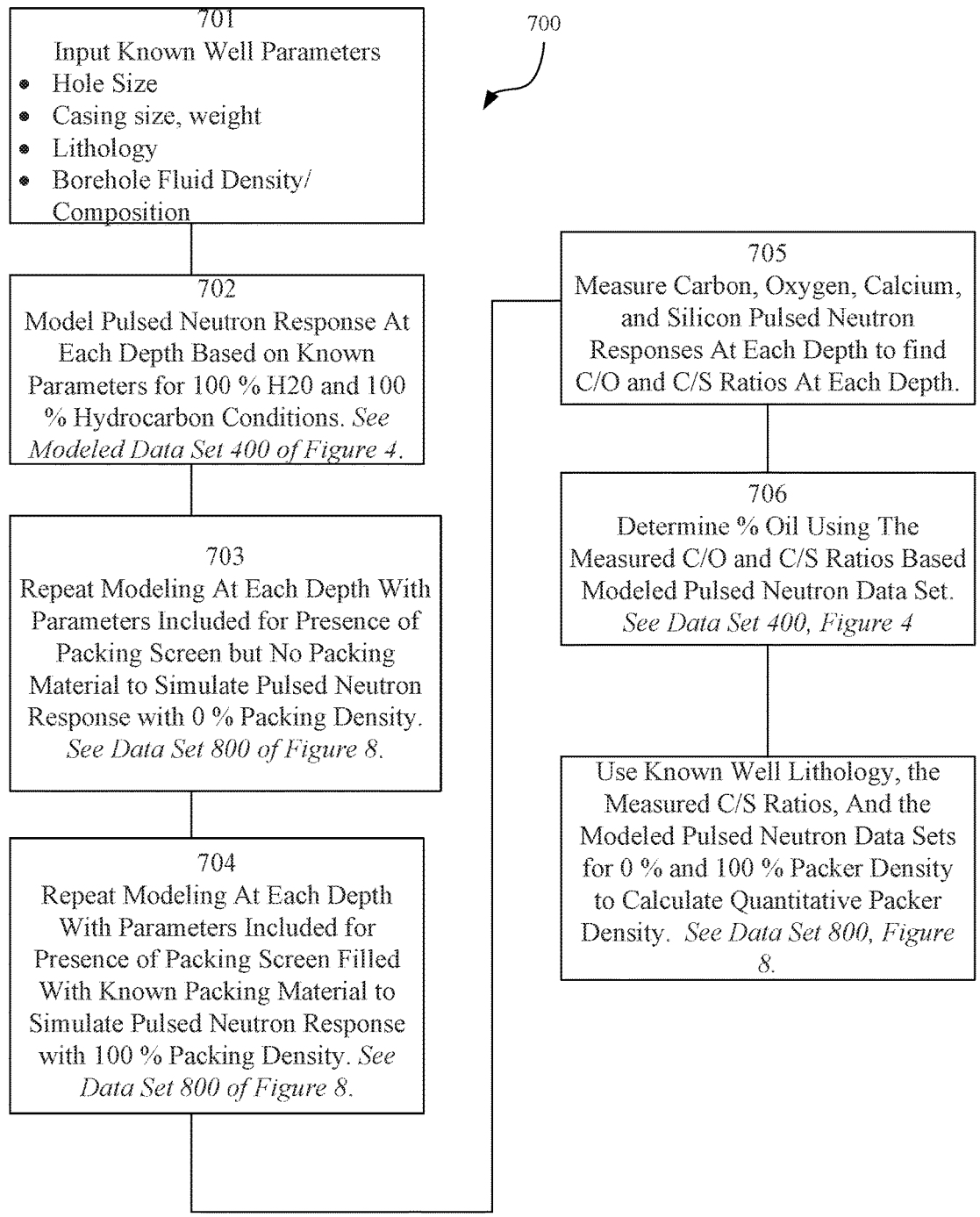
FIG. 7 illustrates a method for determining pack density.

FIG. 7 illustrates a method 700 of gravel pack density determination. As with the pulsed neutron methods described above, method 700 utilizes known parameters 701 of the wellbore, such as hole size, casing size and weight, lithography borehole fluid density and composition, etc. as inputs. Those parameters are known from MWD/LWD measurements, borehole records, etc. The pulsed neutron responses are modeled 702 at each depth (and corresponding lithography/porosity) for both 100% water and 100% hydrocarbon conditions. The pulsed neutron model is then repeated for each depth for a gravel pack density of 0% (703) and of 100% (704). The gravel pack density model can include parameters relating to the known gravel pack material composition, the known screen size and weight, etc. Having modeled the pulsed neutron measurements for the borehole with no pack screen, with a pack screen but 0% pack density, and with 100% pack density, actual pulsed neutron measurements are acquired for the wellbore 705. The oil content of the formation can be determined from the measured C/O and C/S ratios 706, as described above. The gravel pack density can be quantitatively determined 707 by extrapolating between the modeled 0% and 100% density C/S values for the measured C/S value.

Figure 8:
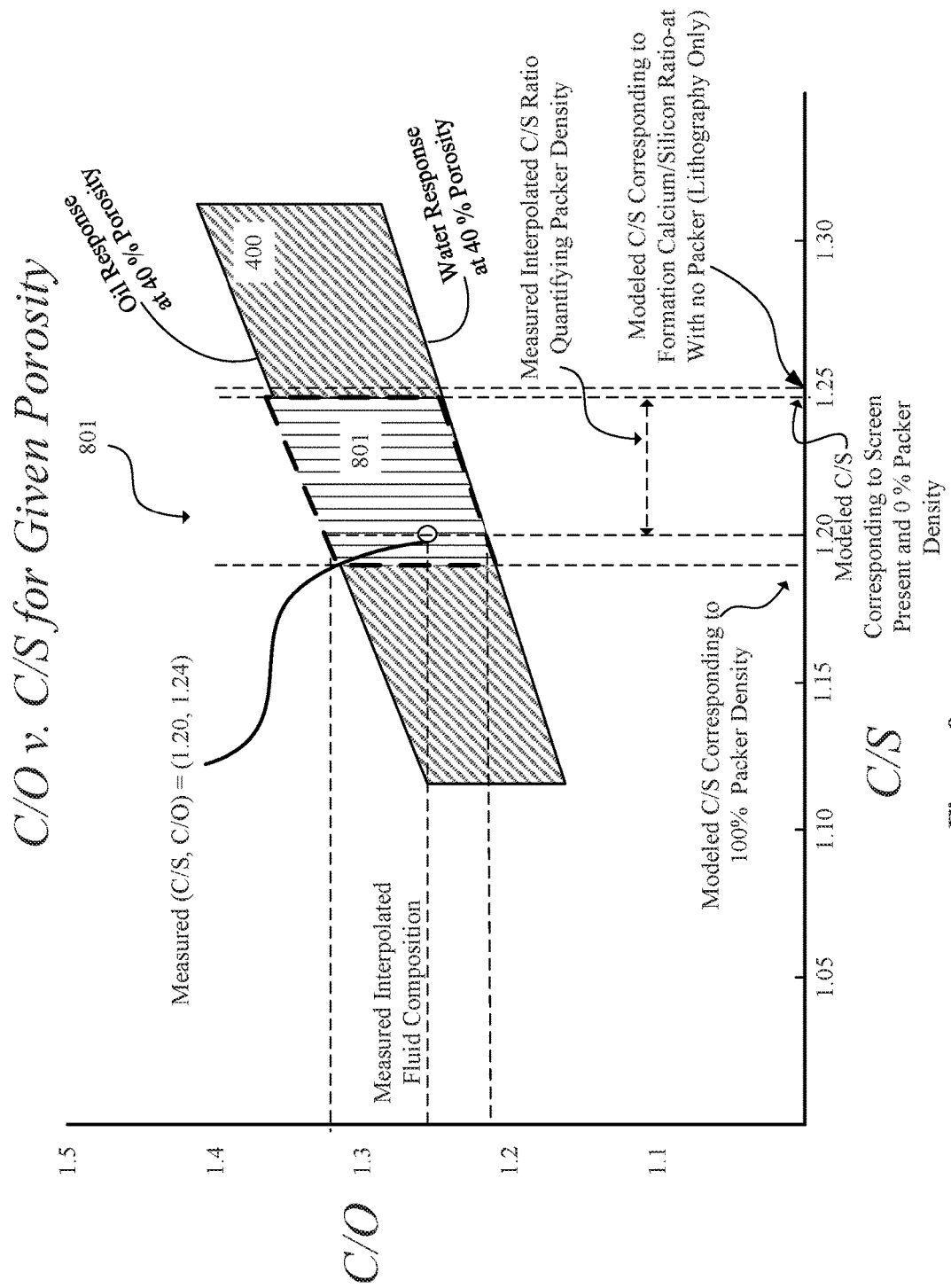
FIG. 8 illustrates modeled data for a formation containing varying pack density.

Implementation of the method 700 will now be discussed with reference to modeled pulsed neutron data 800 illustrated in FIG. 8. Assume that the model 800 represents modeled pulsed neutron measurements for a formation having 40% porosity and identical lithography as the formation modeled 400 of FIG. 4. Repeating the modeling for 0% and 100% gravel pack density yields box 801 corresponding to an area between 0% gravel pack density and 100% gravel pack density. The 0% gravel pack density model yields C/S values close to those of the original model 400. In other words, assume that the known lithography and porosity yields a modeled C/S ratio of 1.25 if no pack or screen is included in the model. The C/S value modeled for that formation porosity and lithography, including a screen but with 0% pack density may be slightly shifted one direction or the other, but is expected to be very close to the value obtained absent any pack considerations. In the illustrated example, the C/S value at 0% pack density is shifted to a slightly lower value, about 1.245 compared to 1.25 modeled with no screen. Also, as expected, the C/S value of the 100% gravel pack density model is shifted to a significantly lower value due to the amounts of calcium and silicon in the packing material. The modeled C/S for 100% pack density is about 1.19 in the illustrated example.

Now assume that actual pulsed neutron measurements yield a C/S value of 1.20. From the model of using known lithography and porosity, the C/S value would be expected to be 1.25, absent any screen or pack considerations. Moreover, with a screen present and 0% packing density the C/S value would be expected to be 1.245. And with a screen present and 100% packing density the C/S value would be expected to be 1.20. Interpolating between the C/S values 1.245 and 1.20 quantitatively yields the actual pack density at the measured location of the wellbore.

Figure 9:
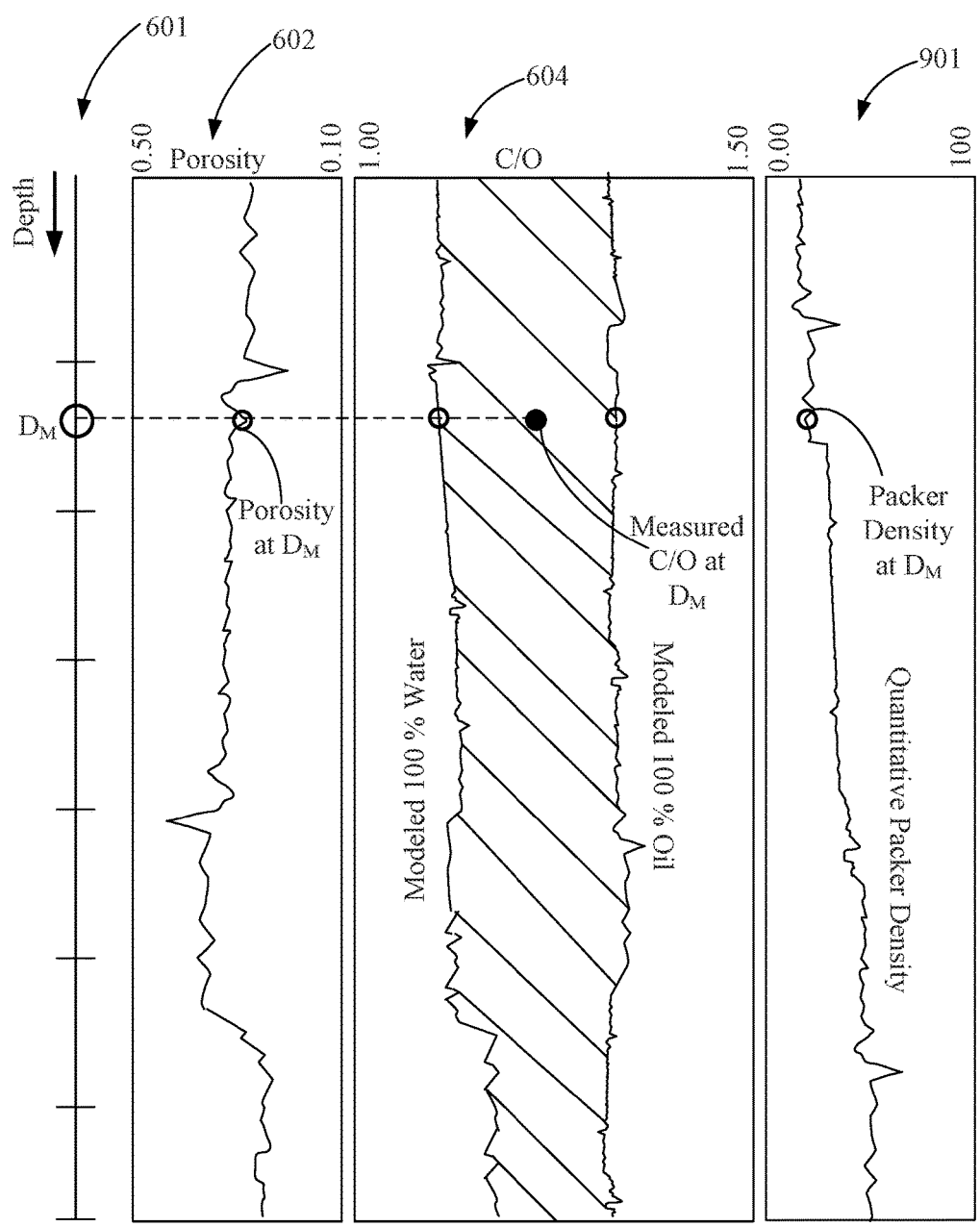
FIG. 9 shows C/O saturation and pack density plotted as a function of depth.

Pack density can be quantitatively determined at each depth of interest using the methods described above. Once determined, the quantitative pack density 901 can be displayed on a depth chart, as illustrated in FIG. 9.

The methods and apparatus described herein can provide quantitative pack density measurements. Moreover, since the pulsed neutron tool can be configured to acquire pulsed neutron measurements for carbon, oxygen, calcium, and silicon, both pack density and hydrocarbon/water saturation can be determined in a single trip of the logging tool.

While the invention herein disclosed has been described in terms of specific embodiments and applications thereof, numerous modifications and variations could be made thereto by those skilled in the art without departing from the scope of the invention set forth in the claims.

What is claimed is:

1. A method for determining gravel pack density within a section of a wellbore in a formation, the method comprising:
providing a first model of pulsed neutron measurements of the section based on a condition in which the section contains a screen and contains zero percent pack density and wherein pores in the formation contain one hundred percent water;
providing a second model of pulsed neutron measurements of the section based on a condition in which the section contains a screen and contains zero percent pack density and wherein the pores in the formation contain one hundred percent hydrocarbon;
providing a third model of pulsed neutron measurements of the section based on a condition in which the section contains a screen and contains one hundred percent pack density and wherein the pores in the formation contain one hundred percent water;
providing a fourth model of pulsed neutron measurements of the section based on a condition in which the section contains a screen and contains one hundred percent pack density and wherein the pores in the formation contain one hundred percent hydrocarbon;
obtaining pulsed neutron measurements, via a pulsed neutron tool, of the section; and
comparing, via a processor, the obtained pulsed neutron measurements to the first, second, third and fourth models to quantify the gravel pack density of the section.

2. The method of claim 1, wherein the first, second, third and fourth models are based on a known porosity and known lithology of the formation in the section.

3. The method of claim 1, wherein the first, second, third and fourth models are based on Monte Carlo simulations.

4. The method of claim 1, wherein providing the first, second, third, and fourth models comprises inputting parameters relating to one or more properties of the section selected from hole size, casing size, casing weight, formation lithography, borehole fluid density, borehole fluid composition, screen weight, and screen composition.

5. The method of claim 1, wherein providing the third and fourth models comprises inputting parameters relating to one or more properties of the section selected from hole size, casing size, casing weight, formation lithography, borehole fluid density, borehole fluid composition, screen weight, screen composition, and pack material composition.

6. The method of claim 5, wherein the parameter relating to pack material composition comprises silicon content of the pack material.

7. The method of claim 1, wherein acquiring puled neutron measurements of the section comprises acquiring pulsed neutron measurements derived from carbon, oxygen, calcium and silicon within the section during a single trip of a pulsed neutron tool.

8. The method of claim 1, wherein each of the first, second, third, and fourth models comprises modeled calcium and silicon measurements.

9. The method of claim 8, wherein the obtained pulsed neutron measurements comprise obtained pulsed neutron measurements for calcium and silicon and wherein quantifying the gravel pack density comprises:
determining a ratio of the obtained pulsed neutron measurements for calcium and for silicon, and
extrapolating the determined ratio of the obtained pulsed neutron measurements for calcium and for silicon with respect to the modeled calcium and silicon measurements.

10. The method of claim 9, wherein each of the first, second, third and fourth models comprises modeled carbon and oxygen measurements.

11. The method of claim 10, wherein the obtained pulsed neutron measurements pulsed neutron measurements further comprise obtained pulsed neutron measurements for carbon and oxygen and wherein the method further comprises determining hydrocarbon saturation in the formation by:
determining a ratio of the obtained pulsed neutron measurements for carbon and oxygen, and
extrapolating the determined ratio of carbon and oxygen with respect to the modeled carbon and oxygen measurements.

12. A system for determining pack density in a section of a formation, the system comprising:
a pulsed neutron tool configured to acquire pulsed neutron measurements derived from calcium silicon, carbon and oxygen within the section; and
a processor configured to:
compare the acquired pulsed neutron measurements derived from calcium and silicon with a first model of pulsed neutron measurements of the section based on a condition in which the section contains a screen and contains zero percent pack density and a second model of pulsed neutron measurements of the section based on a condition in which the section contains a screen and one hundred percent pack density;
calculate pack density based on the comparison; and
compare the acquired pulsed neutron measurements derived from carbon and oxygen with a third model of pulsed neutron measurements of the section based on a condition in which formation pores within the section contain zero percent hydrocarbon and a fourth model of pulsed neutron measurements of the section based on a condition in which formation pores within the section contain one hundred percent hydrocarbon and to determine hydrocarbon saturation based on the comparison.

13. The system of claim 12, wherein the pulsed neutron tool configured to acquire pulsed neutron measurements derived from calcium, silicon, carbon and oxygen during a single trip of the pulsed neutron tool.

* * * * *

UNITED STATES PATENT AND TRADEMARK OFFICE
CERTIFICATE OF CORRECTION

PATENT NO. : 10,215,880 B1
APPLICATION NO. : 15/725051
DATED : February 26, 2019
INVENTOR(S) : Darryl E. Trcka et al.

It is certified that error appears in the above-identified patent and that said Letters Patent is hereby corrected as shown below:

In the Claims

Column 8, Line 4, in Claim 7, after "acquiring," delete "puled" and insert --pulsed--.

Column 8, Lines 25 and 26, in Claim 11, after "obtained," delete duplicate "pulsed neutron measurements".

Signed and Sealed this
Ninth Day of April, 2019

Andrei Iancu
*Director of the United States Patent and Trademark Office*